US 7,494,772 B2

(12) United States Patent
McCready et al.

(10) Patent No.: US 7,494,772 B2
(45) Date of Patent: Feb. 24, 2009

(54) NUCLEOTIDE SEQUENCES SPECIFIC TO YERSINIA PESTIS AND METHODS FOR THE DETECTION OF YERSINIA PESTIS

(75) Inventors: Paula M. McCready, Tracy, CA (US); Lyndsay Radnedge, San Mateo, CA (US); Gary L. Andersen, Berkeley, CA (US); Linda L. Ott, Livermore, CA (US); Thomas R. Slezak, Livermore, CA (US); Thomas A. Kuczmarski, Livermore, CA (US); Vladinir L. Motin, League City, TX (US)

(73) Assignee: Lawrence Livermore National Security, LLC, Livermore, CA (US)

( * ) Notice: Subject to any disclaimer, the term of this patent is extended or adjusted under 35 U.S.C. 154(b) by 691 days.

(21) Appl. No.: 10/630,536

(22) Filed: Jul. 29, 2003

(65) Prior Publication Data

US 2006/0019254 A1    Jan. 26, 2006

Related U.S. Application Data

(60) Provisional application No. 60/400,890, filed on Aug. 1, 2002.

(51) Int. Cl.
*C07H 21/02* (2006.01)
*C07H 21/04* (2006.01)
*C12Q 1/68* (2006.01)

(52) U.S. Cl. .................. 435/6; 536/24.3; 536/24.33; 536/23.1

(58) Field of Classification Search .............. None
See application file for complete search history.

(56) References Cited

U.S. PATENT DOCUMENTS 5,474,796 A * 12/1995 Brennan .............. 427/2.13

5,541,308 A * 7/1996 Hogan et al. .............. 536/23.1

OTHER PUBLICATIONS

Hu et al. "Structural Organization of Virulence-Associated Plasmids of *Yersinia pestis*", J. Bacteriol., Oct. 1998, p. 5192-5202.*
GenBank accession No. AF053947, www.pubmed.com.*
Higgins J. et al "5' Nuclease PCR assay to detect *Yersinia pestis*" Journal OG Clinical Microbiology vol. 36, No. 8 Aug. 1998, pp. 2284-2288 XP009042230.
Iqbal S S et al "Detection of *Yersinia pestis* by Pesticin Fluorogenic Probe-coupled PCR" Molecular and Cellular Probes, Academic Press, London GB vol. 14, No. 2 Apr. 2000 pp. 109-114 XP004435434.
Radnedge L. et al "Identification of Nucleotide Sequences for the Specific and Rapid Detection of *Yersinia pestis*" Applied and Environmental Microbiology vol. 67, No. 8, Aug. 2001 pp. 3759-3762, XP002315805.
Zhang B "Sensitivity and Specificity of FRET probes for the Identification of Three Target Genes of *Yersinia pestis*" Abstracts of the General Meeting of the American Society of Microbiology vol. 102, May 19, 2002 p. 147 XP008042231.
International Search Report, PCT/US2003/024135, Feb. 1, 2005, 4 pages.
International Preliminary Examination Report, PCT/US2003/024135, Jun. 5, 2007, 4 pages.
Prince et al., "*Yersinia pestis* pFra Shows Biovar-Specific Differences and Recent Common Ancestry with a *Salmonella enterica* Serovar Typhi Plasmid," J. Bactriol., Apr. 2001, pp. 2586-2594.

* cited by examiner

*Primary Examiner*—Sarae Bausch
(74) *Attorney, Agent, or Firm*—John H. Lee; Eddie E. Scott

(57) ABSTRACT

Nucleotide sequences specific to *Yersinia pestis* that serve as markers or signatures for identification of this bacterium were identified. In addition, forward and reverse primers and hybridization probes derived from these nucleotide sequences that are used in nucleotide detection methods to detect the presence of the bacterium are disclosed.

9 Claims, No Drawings

NUCLEOTIDE SEQUENCES SPECIFIC TO YERSINIA PESTIS AND METHODS FOR THE DETECTION OF YERSINIA PESTIS

RELATED APPLICATION

This application claims the benefit of U.S. Provisional Application No. 60/400,890 filed Aug. 1, 2002, and entitled, "DNA Diagnostics Yersinia Pestis and Methods for the Detection of Yersinia Pestis" which is incorporated herein by reference.

The United States Government has rights in this invention pursuant to Contract No. W-7405-ENG-48 between the United States Department of Energy and the University of California for the operation of Lawrence Livermore National Laboratory.

GENE SEQUENCE LISTING IN COMPUTER READABLE FORM

The sequence listing information recorded in computer readable form is identical to the written on paper sequence listing.

BACKGROUND

Yersinia Pestis is the species of bacteria known to cause the plague, a highly contagious and often fatal disease. Since the attack on the World Trade Center in New York of Sep. 11, 2001, there has been a growing concern that terrorists or rogue governments will use the Yersinia pestis bacterium as a weapon of mass destruction and instrument of terror. Since the events of Sep. 11, 2001, the United States Government has been developing reliable methods and systems to detect the Yersinia pestis bacterium so that immediate and effective counter measures can be undertaken. The existing methods for detecting the Yersinia pestis bacterium are considered inadequate because of the higher than acceptable rate of false positive and false negative results. False positive results lead to confusion regarding whether the Yersinia pestis bacterium is actually present and whether protective measures should immediately be implemented. Conversely, false negative results would allow the Yersinia pestis bacterium to remain undetected with consequent adverse impacts. A more reliable method of detecting the Yersinia pestis bacterium would reduce the occurrence of false positive and false negative results and provide decision makers with greater confidence in implementing appropriate counter measures.

SUMMARY OF THE INVENTION

This invention includes the nucleotide sequences that are identified in SEQ ID NOs 4, 8, 12, 16, 20 and 24 that are specific to Yersinia pestis.

Another aspect of the invention includes a Forward Primer, the nucleotide sequences that are identified in SEQ ID Nos 1, 5, 9, 13, 17 and 21, and any primers that are derived from these nucleotide sequences.

A further aspect of the invention includes a Reverse Primer, the nucleotide sequences that are identified in SEQ ID NOs 2, 6, 10, 14, 18 and 22, and any primers that are derived from these nucleotide sequences.

A further aspect of the invention includes a Hybridization Probe, the nucleotide sequences that are identified in SEQ ID NOs 3, 7, 11, 15, 19 and 23, and any probes that are derived from these nucleotide sequences.

This invention also includes a method for the detection of Yersinia pestis using the bacterium specific nucleotide sequence comprising: providing a sample in an environment that is suitable for isolating genomic DNA for amplification using PCR and under conditions suitable for hybridization with a least one group of nucleotides consisting of a forward primer, a reverse primer and a hybridization probe and detecting the existence of Yersinia pestis specific nucleotide sequences by a nucleotide detection method, such as PCR and flurogenic 5' nuclease PCR assay, wherein the existence of the nucleotide sequence indicates the presence of Yersinia pestis in the sample.

BRIEF DESCRIPTION OF THE SEQUENCE SETS

| | |
|---|---|
| SEQ ID NO:1 | Primer |
| SEQ ID NO:2 | Primer |
| SEQ ID NO:3 | Probe |
| SEQ ID NO:4 | Amplicon |
| SEQ ID NO:5 | Primer |
| SEQ ID NO:6 | Primer |
| SEQ ID NO:7 | Probe |
| SEQ ID NO:8 | Amplicon |
| SEQ ID NO:9 | Primer |
| SEQ ID NO:10 | Primer |
| SEQ ID NO:11 | Probe |
| SEQ ID NO:12 | Amplicon |
| SEQ ID NO:13 | Primer |
| SEQ ID NO:14 | Primer |
| SEQ ID NO:15 | Probe |
| SEQ ID NO:16 | Amplicon |
| SEQ ID NO:17 | Primer |
| SEQ ID NO:18 | Primer |
| SEQ ID NO:19 | Probe |
| SEQ ID NO:20 | Amplicon |
| SEQ ID NO:21 | Primer |
| SEQ ID NO:22 | Primer |
| SEQ ID NO:23 | Probe |
| SEQ ID NO:24 | Amplicon |

DETAILED DESCRIPTION

Disclosed herein are six nucleotide sequences located on different loci of the Yersinia pestis bacterium genome. Also disclosed, are primers and the hybridization probes used in detecting the specific nucleotide sequences as well as method for identifying Yersinia pestis by analyzing samples taken from monitoring devices, such as air monitors, for the nucleotide sequences that are specific to Yersinia pestis. By using the primers and hybridization probes developed from the nucleotide sequences identifies as unique to the Yersinia Pestis bacterium to detect the presence of the Yersinia pestis bacterium, far more reliable results are obtained than by using existing methods. False positive and false negative results are also greatly reduced.

Yersinia Pestis is the bacterium that causes what is commonly known as the plague, a disease that is contagious and can be fatal if not detected early and treated with appropriate antibiotics. The symptoms of plague "are fever, headache, weakness, and rapidly developing pneumonia with shortness of breath, chest pain, cough, and sometimes bloody or watery sputum. The pneumonia progresses for 2 to 4 days and may cause respiratory failure and shock." This information can be found at the website for the Center for Disease Control and Prevention (CDC). It is on the Center for Disease Control and Prevention (CDC) list of possible bacteria that has potential as a biological warfare weapon. The CDC has developed a list of possible pathogens that may be used as bioterrorism weapons. *Yersinia Pestis* has been listed in Category A of possible diseases and agents. Those diseases and agents in Category A are considered a high risk to national security because they "can be easily disseminated or transmitted from person to person; result in high mortality rates and have the potential for major public health impact; might cause public panic and social disruption; and require special action for public health preparedness." This information can be found at the CDC website.

A key element in developing defenses against the use of *Yersinia pestis* is the ability to quickly and accurately detect the presence of the bacterium. Early detection will allow for the implementation of effective counter measures. Additionally, early detection will allow for the identification and treatment of those that may have been exposed to the bacterium. Early detection and treatment is essential for the treatment of Plague because significant adverse health effects, including death, may occur if it is not detected early and treated with antibiotics.

Existing detection methods have resulted in a higher than acceptable rate of false positive and false negative results. Such results are inadequate and can create confusion regarding the appropriate countermeasures, if any, that should be undertaken because it is unclear whether the bacterium is present or not. If the bacterium is not present, undertaking counter measures may cause undue expense and create unwarranted concern among those that may incorrectly believe they have been exposed.

Although the genome for *Yersinia pestis* has already been mapped, this alone was not sufficient to develop a reliable and accurate detection mechanism because the current methods use nucleotide sequences that may be common to many different bacteria. Thus, existing detection methods could not distinguish between various bacteria, which resulted in higher than acceptable false positive detection rates. Similarly, some existing detection methods resulted in false negative results because they were not sensitive enough to detect the bacterium. Using a nucleotide sequence that is specific to the *Yersinia pestis* bacterium results in a move reliable detection method.

Six nucleotide sequences contained in SEQ ID Nos 4, 8, 12, 16, 20 and 24 that are specific to the *Yersinia pestis*. These sequences are known as "amplicons." The existence of these nucleotide sequences in a sample is proof that the bacterium *Yersinia pestis* is present. In order to detect any of the six amplicons specific to *Yersinia pestis*, a series of forward and reverse primers and hybridization probes were developed for each of the six amplicons.

The typical assay determines the presence of SEQ ID Nos 4 and 8 using the sequence specific primers and the hybridization probes. If there is a positive result for the presence of *Yersinia pestis* then an assay is run to determine the presence of additional amplicon sequences, as a means to double check for the presence of *Yersinia pestis*.

Once the *Yersinia pestis* specific nucleotide sequences were identified, the presence of the bacteria could be detected from environmental samples using PCR assay analysis and detection. PCR is a technique utilized to amplify genomic DNA. Typical PCR reactions include appropriate PCR buffers, nuclease polymerase and one or more oligonucleotide primers and hybridization probes. Various modifications of PCR techniques are possible as detailed in *Current Protocols in Molecular Biology* ed. F. M. Ausubel, R. Brent, D. D. Moore, K. Struhle, Massachusetts General Hospital and Harvard Medical School (1987), which is hereby incorporated by reference. The following US patents describe PCR and are incorporated herein by reference: U.S. Pat. Nos. 4,683,195; 4,683,202; 4,800,159.

One method that may be used for real-time PCR amplification and detection is TaqMan®. The principles involved in the conventional Taqman® 5' exonuclease assay are described in detail by Holland et al in, *Detection of specific polymerase chain reaction product by utilizing the 5' - - - 3' exonuclease activity of Thermus aquaticus polynucleotide polymerase*, Proc Natl Acad Sci U S A 88 (16):7276-80, 1991, which is herein incorporated by reference. TaqMan® real time detection can also be used to simultaneously detect a plurality of nucleic acid targets when it is used with multiplex PCR, which enables simultaneous detection of more than one target sequence, thus enhancing detection accuracy. A few examples of typical PCR instruments include the ABI prism 7700, the Cepheid Smart Cycler, and the Bio-Rad iCycler. In order to use a PCR assay method for detection of the *Yersinia pestis* bacterium, the sample must be prepared to extract all DNA that may be present. The following is a protocol for the preparation of samples taken from ambient air monitoring devices for nucleotide detection using fluorogenic 5' nuclease PCR assay.

Assay Protocol

Definitions:
   DNA—deoxyribonucleic acid
   EDTA—ethylenediaminetetraacetic acid
   PCR—polymerase chain reaction
   PCR water—autoclaved water, then filtered
   CT—cycle threshold—the cycle in which the fluorescence signal crosses a user defined threshold
   FAM—reporter dye
   TAMRA—quencher dye Sample Preparation:
Exposed environmental filter are suspended in Sodium phosphate/EDTA, Tween buffer and bead beaten. The supernatant is filtered and washed to yield the genomic DNA extract. The extract is then subjected to real-time polymerase chain reaction (PCR) assay using a fluorescent-labeled probe. This process monitors a PCR reaction and the quantity of double-stranded product that is produced Materials Needed:
1. A series of forward and reverse primers, a hybridization probe and polymerase reagents specific to the first amplicon to be detected.
2. A series of forward and reverse primers, a hybridization probe and polymerase reagents specific to the second amplicon to be detected.

Bead beater Kit includes:
   a. 3 capped tubes containing a filter and beads
   b. 3 yellow ultra free MC Centrifugal Filter Units
   c. 6 blue microcon YM-100 filter units
   d. 12 collection tubes
   e. 7 PCR reaction mix—includes primer/probe and Taq—labeled A, B, C, D, E, F, G
   f. 48-25 µl Smart Cycle reaction tubes
   g. Sodium phosphate buffer/EDTA Teen buffer
   h. PCR water
   i. Inhibitory control DNA
   j. Extra unlabeled tubes
3. Cepheid Smart Cycle
4. Microcentrifuge
5. Microfuge for Cepheid tubes Preparation of DNA Extract:

This part of the assay protocol should be perform in segregated work areas and in a biosafety cabinet using BSL 2 practices.

1. Add 400 μl of Sodium phosphate/EDTA Teen buffer to each of the capped tubes containing a filter and beads. Screw cap tightly.
2. Insert tubes one at a time into the bead beater.
3. Bead beat the capped tube for 3 minutes and a speed of 5000 rpm.
4. Remove capped tube from bead beater and place the tube on ice for a minimum of 2 minutes to cool.
5. Wash Steps.
   Spin capped filter tubes for 10 seconds (pulse spin) in microcentrifuge.
   Transfer approximately 400 μl of the supernatant to the yellow top filter collection tube.
   Spin the yellow top filter tube with the supernatant @7000 rpm for 3 minutes.
   Transfer the filtered liquid to a blue microcon filter on collection tube #1.
   Spin @7000 rpm for 1 minute. Check fluid level in the blue microcon filter. If it is above the white base, pulse spin for about 10 seconds to bring the level at or a little below the white area. Several pulse spins may be necessary to bring the level down. This is approximately 100-200 μl of liquid.
   Transfer this liquid on the top of the filter to a second blue microcon filter on a clean collection tube #2. Tilt the tube at a 45° angle and take off the liquid—do NOT vacuum the filter.
   Add 400 μl of PCR water to the second blue microcon filter with the added liquid.
   Spin@7000 rpm for 2 minutes. Do not be spin dry Approximately 50-100 μl of liquid should be on top of the filter. Pulse spin if the level is too high
   Using clean, metal forceps remove the blue microcon filter from the collection tube #2 and place the blue microcon filter on a clean collection tube #3. Discard collection tube #2.
   Add 400 μl PCR water to the blue microcon filter on collection tube #3.
   Spin @7000 rpm for 2 minutes. Do not be spin dry; approximately 50-100 μl of liquid should be on top of the filter. Pulse spin if the level is too high.
   Remove the blue microcon filter. Place the blue microcon filter on collection tube #4. Discard collection tube #3
   Add 400 μl PCR water to the blue microcon filter on collection tube #4.
   Spin for 1 minute @7000 rpm. Check fluid level in the blue microcon filter. If it is above the white base, pulse spin for about 10 seconds to bring the level at or a little below the white area. Several pulse spins may be necessary. If the level of liquid is at or a little below the white base, there is approximately 100-200 μl of DNA extract. If for some reason the pulse spin has brought the level of DNA extract down too low add 200 μl PCR water and bring the level carefully to the white base level by pulse spinning for less time.
   Transfer the liquid on the top of the blue microcon filter (i.e., the DNA extract) to the eppendorf tube.
   If the PCR assay cannot be performed immediately, keep extract refrigerated.

PCR Assay:
1. Thaw on ice each set of primer/probe/Taq polymerase sets. Once thawed PCR assay must begin. Do NOT refreeze. Keep on ice while testing.
2. Add 20 μl of each of the PCR reaction mixes for each amplicon and one inhibitory control to the appropriately labeled Cepheid reaction tubes; e.g. 1-1A is for amplicon 1, filter 1, a set of primers, probe, Taq polymerase.
   a. Add 5 μl of DNA extract to each of the tubes—rinse tip 1-2 times in the mix and discard the tip.
   b. Use a clean tip for each reaction tube.
   c. Each tube should have a total of 25 μl.
3. Add 15 μl of PCR reaction inhibitory mix to appropriately labeled Cepheid tubes; e.g, INHIB.
   a. Add 5 μl DNA extract to each tube—rinse tip 1-2 times in the mix and discard tip.
   a. Add 5 μl of DNA inhibitory control to each tube—rinse tip 1-2 times in the mix and discard the tip.
   a. Use a clean tip for each reaction tube.
   b. Each tube should have a total of 25 μl.
4. Include as controls:
   NTC (no template control) for each set of primers/probe, Taq.
5. Spin Cepheid tubes in Cepheid microfuge for about 4 seconds. This mixes the PCR reaction mix and DNA into the optic diamond area. Check to see that the optic area is filled.
6. Run Cepheid Smart Cycler
7. Record all CT values (including 0) on the result sheet for the appropriate organism and filter. CT values equal to 34 to 35 indicate negative readings—no *Yersinia pestis* detected. CT values below 34 indicate a positive reading—*Yersinia pestis* DNA detected.

TABLE 1

*yersinia pestis* environmental soil samples

|  | *Y. pestis*-kim DNA/Positive Control | Environmental Soil Sample D4 | | D36 | | D65 | |
| --- | --- | --- | --- | --- | --- | --- | --- |
|  |  | run1 | run2 | run1 | run2 | run1 | run2 |
| Seq. ID No. 1, 2, 3 | 23.28 | 35 | 35 | 35 | 35 | 35 | 35 |
| Seq. ID No 5, 6, 7 | 20.28 | 35 | 35 | 35 | 35 | 35 | 35 |
| Seq. ID No. 9, 10, 11 | 19.78 | 35 | 35 | 34.43 | 35 | 35 | 35 |
| Seq. ID No. 13, 14, 15 | 20.17 | 35 | 35 | 35 | 35 | 35 | 35 |
| Seq. ID No. 17, 18, 19 | 32.57 | 35 | 35 | 35 | 35 | 35 | 35 |
| Seq. ID No. 21, 22, 23 | 22.26 | 35 | 35 | 35 | 35 | 35 | 35 |

TABLE 1-continued

*yersinia pestis* environmental soil samples

| | Y. pestis-kim DNA/Positive Control | Environmental Soil Sample D411 | | D425 | | D428 | |
|---|---|---|---|---|---|---|---|
| | | run1 | run2 | run1 | run2 | run1 | run2 |
| Seq. ID No. 1, 2, 3 | 23.28 | 35 | 35 | 35 | 35 | 35 | 35 |
| Seq. ID No 5, 6, 7 | 20.28 | 35 | 35 | 35 | 35 | 35 | 35 |
| Seq. ID No. 9, 10, 11 | 19.78 | 35 | 35 | 35 | 35 | 35 | 35 |
| Seq. ID No. 13, 14, 15 | 20.17 | 35 | 35 | 35 | 35 | 35 | 35 |
| Seq. ID No. 17, 18, 19 | 32.57 | 35 | 35 | 35 | 35 | 35 | 35 |
| Seq. ID No. 21, 22, 23 | 22.26 | 35 | 35 | 35 | 35 | 35 | 35 |

Table 1 shows the results of assay runs that were performed using the above described protocol. An assay set containing the primers and probe for each amplicon sequence was added to a sample containing either the *Yersinia pestis* DNA or an environmental soil sample. The environmental soil samples were used as controls to demonstrate that the primers and probes derived from the *Yersinia pestis* specific amplicon could identify the *Yersinia pestis* bacterium, thereby demonstrating the specificity of the amplicon sequence. The *Yersinia pestis* DNA was obtained from American Type Culture Collection. The assay sets containing the probes and primers were obtained from various vendors such as ABI and Biosearch.

Some assays were run twice for a specific environmental soil sample, while some assays were only run once. The results show that the assay runs having the *Yersinia pestis* DNA in the sample had positive results, CT values of less than 34. Those assay runs with environmental soil samples had negative results, CT values of 34 to 35, an expected result given that *Yersinia pestis* bacterium would not be expected to be present in a soil sample. These results show that the primers and probes derived from the *Yersinia pestis* specific amplicon can distinguish between DNA from the *Yersinia pestis* bacterium and DNA that may be contained in environmental soil samples, thereby, demonstrating that the nucleotide sequences in the amplicons are specific to *Yersinia pestis* and that false positive results should not occur using these assays in the field.

The inventions disclosed herein are based on nucleotide sequences that are specific to *Yersinia pestis*. Accordingly, although air monitors are an effective method of obtaining samples for analyses, a wide variety of other media and methods may be used to provide the samples for analysis for the *Yersinia pestis* bacterium and this invention is not limited by the method or media from which a sample for analysis is obtained.

All numbers expressing quantities of ingredients, constituents, reaction conditions, and so forth used in the specification and claims are to be understood as being modified in all instances by the term "about". Notwithstanding that the numerical ranges and parameters setting forth the broad scope of the subject matter presented herein are approximations, the numerical values set forth in the specific examples are reported as precisely as possible. Any numerical value, however, inherently contain certain errors necessarily resulting from the standard deviation found in their respective testing measurements.

All publications and patents mentioned in the above specification are herein incorporated by reference. Various modifications and variations of the described method and system of the invention will be apparent to those skilled in the art without departing from the scope and spirit of the invention. Although the invention has been described in connection with specific preferred embodiments, it should be understood that the invention as claimed should not be unduly limited to such specific embodiments. Indeed, various modifications of the described modes for carrying out the invention which are obvious to those skilled in molecular biology or related fields are intended to be within the scope of the following claims.

The invention claimed is:

1. A set of polynucleotides comprising a first isolated polynucleotide and a second isolated polynucleotide, wherein the first isolated polynucleotide consists of SEQ ID NO:4 or the complement thereof and the second isolated polynucleotide consists of SEQ ID NO:8 or the complement thereof.

2. The set of polynucleotides of claim 1 further comprising at least one isolated polynucleotides consisting of the nucleic acid sequence selected from the group consisting of SEQ ID NOS: 12, 16, 20, and 24 or the complement thereof.

3. The set of polynucleotides of claim 2, comprising six isolated polynucleotides each consisting of one of SEQ ID NOS: 4, 8, 12, 16, 20, and 24 or the complements thereof.

4. The set of polynucleotides of claim 1, further comprising at least one isolated polynucleotides consisting of the nucleic acid sequence selected from the group consisting of SEQ ID NOS: 1, 2, 3, 5, 6, and 7.

5. The set of polynucleotides of claim 2, further comprising at least one isolated polynucleotide consisting of the nucleic acid sequence selected from the group consisting of SEQ ID NOS: 1, 2, 3, 5, 6, 7, 9, 10, 11, 13, 14, 15, 17, 18, 19, 21 ,22, and 23.

6. A method for detection of *Yersinia pestis* in a sample comprising:

(a) providing a sample; and (b) performing a PCR assay to detect the set of polynucleotides of claim 1 in the sample, wherein the detection of a first isolated polynucleotide and a second isolated polynucleotide indicates the presence of *Yersinia pestis* in the sample, wherein the first isolated polynucleotide consists of SEQ ID NO: 4 or the complement thereof and the second isolated polynucleotides consists of SEQ ID NO: 8 or the complement thereof.

7. The method of claim 6, wherein said PCR comprises standard PCR.

8. The method of claim 7, wherein said standard PCR comprises fluorogenic 5' nuclease PCR assay.

9. The method of claim 6, wherein said assay is performed using a first forward primer consisting of SEQ ID NO: 1, a first reverse primer consisting of SEQ ID NO: 2, and a first hybridization probe consisting of SEQ ID NO: 3 for the detection of SEQ ID NO: 4 and using a second forward primer consisting of SEQ ID NO: 5, a second reverse primer consisting of SEQ ID NO: 6, and a second hybridization probe consisting of SEQ ID NO: 7 for detection of SEQ ID NO: 8 and detecting the presence of SEQ ID NO: 4 and SEQ ID NO: 8 by fluorogenic 5' nuclease PCR assay, wherein the presence of SEQ ID NO: 4 and SEQ ID NO: 8 indicates the presence of *Yersinia pestis* in the sample.

* * * * *

SEQUENCE LISTING

```
<160> NUMBER OF SEQ ID NOS: 24

<210> SEQ ID NO 1
<211> LENGTH: 28
<212> TYPE: DNA
<213> ORGANISM: Yersinia Pestis

<400> SEQUENCE: 1
atttcccacc aatcaacgat acaagaat                                    28

<210> SEQ ID NO 2
<211> LENGTH: 28
<212> TYPE: DNA
<213> ORGANISM: Yersinia Pestis
```

<400> SEQUENCE: 2
ccatgttcat gttatgtcca ccaacaag                                          28

<210> SEQ ID NO 3
<211> LENGTH: 33
<212> TYPE: DNA
<213> ORGANISM: Yersinia pestis

<400> SEQUENCE: 3
catggaatca cacaaaaata atggcctcag atg                                    33

<210> SEQ ID NO 4
<211> LENGTH: 102
<212> TYPE: DNA
<213> ORGANISM: Yersinia Pestis

<400> SEQUENCE: 4
atttcccacc aatcaacgat acaagaatga catggaatca cacaaaaata atggcctcag       60
atggtactga agctcttgtt ggtggacata acatgaacat gg                         102

<210> SEQ ID NO 5
<211> LENGTH: 24
<212> TYPE: DNA
<213> ORGANISM: Yersinia psetis

<400> SEQUENCE: 5
atttgtcgga aggtcgcagt gaga                                              24

<210> SEQ ID NO 6
<211> LENGTH: 23
<212> TYPE: DNA
<213> ORGANISM: Yersinia pestis

<400> SEQUENCE: 6
cgtcgatgac tttctgacgg cac                                               23

<210> SEQ ID NO 7
<211> LENGTH: 33
<212> TYPE: DNA
<213> ORGANISM: Yersinia pestis

<400> SEQUENCE: 7
cgagatagcc ctgataacgc ttcacagtat ggc                                    33

<210> SEQ ID NO 8
<211> LENGTH: 147
<212> TYPE: DNA
<213> ORGANISM: Yersinia pestis

<400> SEQUENCE: 8
atttgtcgga aggtcgcagt gagaacgaga tagccctgat aacgcttcac agtatggctg       60
tcgcacacca caaccatctt tttgcctcga gggttcgtcc agtagaacga ctcaacggcc      120
gcgcgtgccg tcagaaagtc atcgacg                                          147

<210> SEQ ID NO 9
<211> LENGTH: 22
<212> TYPE: DNA
<213> ORGANISM: Yersinia pestis

<400> SEQUENCE: 9
ttcaagtgct caaagcactg cg                                              22

<210> SEQ ID NO 10
<211> LENGTH: 19
<212> TYPE: DNA
<213> ORGANISM: Yersinia pestis

<400> SEQUENCE: 10
tgaaagggca gcaaccgga                                                  19

<210> SEQ ID NO 11
<211> LENGTH: 31
<212> TYPE: DNA
<213> ORGANISM: Yersinia pestis

<400> SEQUENCE: 11
atattgcccc aacaccacaa caggaatcgt c                                    31

<210> SEQ ID NO 12
<211> LENGTH: 161
<212> TYPE: DNA
<213> ORGANISM: Yersinia pestis

<400> SEQUENCE: 12
tgaaagggca gcaaccggaa ataaaaagca aattaccggc gacaacgcct tgggagtatg     60
gtccgatagc tgctggtgcg ttttgagttt taataatcat tcgacgattc ctgttgtggt    120
gttggggcaa tatttatcac gcagtgcttt gagcacttga a                        161

<210> SEQ ID NO 13
<211> LENGTH: 23
<212> TYPE: DNA
<213> ORGANISM: Yersinia pestis

<400> SEQUENCE: 13
ccacgaataa acgaatgccc aac                                             23

<210> SEQ ID NO 14
<211> LENGTH: 24
<212> TYPE: DNA
<213> ORGANISM: Yersinia pestis

<400> SEQUENCE: 14
tgcgcagata gttattgccg tctt                                            24

<210> SEQ ID NO 15
<211> LENGTH: 30
<212> TYPE: DNA
<213> ORGANISM: Yersinia pestis

<400> SEQUENCE: 15
catagcgcca atggccacaa tcacaaaaag                                      30

<210> SEQ ID NO 16
<211> LENGTH: 177
<212> TYPE: DNA
<213> ORGANISM: Yersinia pestis

<400> SEQUENCE: 16
tgcgcagata gttattgccg tctttcagac gggtcaaatc aacgttattg ccacgtttag     60
aagcaatatc gccacgggtc ttgttaagca gatcaagtaa tgacttagac atgtatttct    120 ccttttgtg attgtggcca ttggcgctat gcgcgttggg cattcgttta ttcgtgg       177

<210> SEQ ID NO 17
<211> LENGTH: 22
<212> TYPE: DNA
<213> ORGANISM: Yersinia pestis

<400> SEQUENCE: 17
gcatgaccga aacgtcatcc tg                                              22

<210> SEQ ID NO 18
<211> LENGTH: 25
<212> TYPE: DNA
<213> ORGANISM: Yersinia pestis

<400> SEQUENCE: 18
tcgtctgtca ttctctgata ggcga                                           25

<210> SEQ ID NO 19
<211> LENGTH: 28
<212> TYPE: DNA
<213> ORGANISM: Yersinia pestis

<400> SEQUENCE: 19
tcggcttcac gactgaggtc tgcatcat                                        28

<210> SEQ ID NO 20
<211> LENGTH: 183
<212> TYPE: DNA
<213> ORGANISM: Yersinia pestis

<400> SEQUENCE: 20
gcatgaccga aacgtcatcc tgaaggctag gcagctcggc ttcacgactg aggtctgcat     60
cattcagttg gacttagcca tattccacag gaaagagtgc gcattgattg cccatactcg    120
gcctgacgca gaaagactct ttcgtaacaa gacgcagttc gcctatcaga gaatgacaga    180
cga                                                                  183

<210> SEQ ID NO 21
<211> LENGTH: 22
<212> TYPE: DNA
<213> ORGANISM: Yersinia pestis

<400> SEQUENCE: 21
catcttctga aggttccggt gc                                              22

<210> SEQ ID NO 22
<211> LENGTH: 21
<212> TYPE: DNA
<213> ORGANISM: Yersinia pestis

<400> SEQUENCE: 22
ctttcagagc ggcaatgatc g                                               21

<210> SEQ ID NO 23
<211> LENGTH: 27
<212> TYPE: DNA
<213> ORGANISM: Yersinia pestis

<400> SEQUENCE: 23
ttcatctctg caatcgcctc acgcagc                                         27

<210> SEQ ID NO 24

-continued

```
<211> LENGTH: 190
<212> TYPE: DNA
<213> ORGANISM: Yersinia pestis

<400> SEQUENCE: 24
catcttctga aggttccggt gcgttcatct ctgcaatcgc ctcacgcagc tgcgtcgccc     60
attctggctc cgggaagccc tgggcaattt cggtatccac tacatccagc gcagcgttgg    120
ccgcgtcata cagtttttc acgtttttc tcctgcatca aaagaaacac gatcattgcc    180
gctctgaaag                                                           190
```